United States Patent
Lundahl

(10) Patent No.: US 10,029,116 B2
(45) Date of Patent: *Jul. 24, 2018

(54) METHOD FOR THE TREATMENT OF ACNE

(71) Applicant: DUSA PHARMACEUTICALS, INC., Wilmington, MA (US)

(72) Inventor: Scott Lundahl, Wilmington, MA (US)

(73) Assignee: DUSA PHARMACEUTICALS, INC., Wilmington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/207,405

(22) Filed: Jul. 11, 2016

(65) Prior Publication Data

US 2016/0317831 A1  Nov. 3, 2016

Related U.S. Application Data

(63) Continuation of application No. 13/963,036, filed on Aug. 9, 2013, now Pat. No. 9,387,341.

(60) Provisional application No. 61/681,888, filed on Aug. 10, 2012.

(51) Int. Cl.
*A61N 5/06* (2006.01)
*A61K 41/00* (2006.01)
*A61K 9/00* (2006.01)

(52) U.S. Cl.
CPC ............ *A61N 5/062* (2013.01); *A61K 9/0014* (2013.01); *A61K 41/0061* (2013.01); *A61N 5/0616* (2013.01); *A61N 2005/0662* (2013.01)

(58) Field of Classification Search
CPC .................. A61N 5/062; A61N 5/0616; A61N 2005/0658; A61N 2005/0661; A61N 2005/0662; A61K 9/0012; A61K 9/0014; A61K 41/0057; A61K 41/0061; A61K 41/0066

USPC ....................... 607/88–91; 606/3, 9; 128/898
See application file for complete search history.

(56) References Cited

U.S. PATENT DOCUMENTS

| | | | | |
|---|---|---|---|---|
| 7,723,910 | B2 * | 5/2010 | Lundahl | A61N 5/062 313/485 |
| 8,216,289 | B2 * | 7/2012 | Lundahl | A61N 5/062 600/476 |
| 9,339,540 | B2 * | 5/2016 | Lundahl | A61K 41/0061 |
| 9,387,341 | B2 * | 7/2016 | Lundahl | A61N 5/062 |
| 9,561,276 | B2 * | 2/2017 | Lundahl | A61K 41/0061 |
| 2003/0093057 | A1 * | 5/2003 | Zhang | A61M 31/002 604/500 |
| 2005/0075703 | A1 * | 4/2005 | Larsen | A61N 1/40 607/88 |
| 2007/0179482 | A1 * | 8/2007 | Anderson | A61B 18/203 606/9 |
| 2008/0188558 | A1 * | 8/2008 | Godal | A61K 31/197 514/529 |
| 2009/0198173 | A1 * | 8/2009 | Samuel | A61N 5/062 604/20 |
| 2009/0259167 | A1 * | 10/2009 | Sakamoto | A61K 31/197 604/21 |
| 2014/0010761 | A1 * | 1/2014 | Parent | C07C 229/22 424/9.6 |
| 2014/0067024 | A1 * | 3/2014 | Jones | A61N 5/062 607/90 |

* cited by examiner

*Primary Examiner* — Ahmed Farah
(74) *Attorney, Agent, or Firm* — Matthew S. Gibson; Ryan P. Cox; Reed Smith LLP

(57) ABSTRACT

This application is directed to a method of treating a patient with acne by applying a photodynamic agent to skin having acne lesions, waiting at least 12 hours, and then exposing the skin to which the photodynamic agent has been applied to light that causes an activation reaction.

18 Claims, No Drawings

METHOD FOR THE TREATMENT OF ACNE

RELATED APPLICATION

This application is a continuation of U.S. patent application Ser. No. 13/963,036, filed on Aug. 9, 2013 which claims priority of U.S. Patent Application Ser. No. 61/681,888, entitled METHOD FOR THE TREATMENT OF ACNE, filed Aug. 10, 2012, the entire disclosure of each is hereby incorporated by reference as if being set forth in its entirety herein.

FIELD OF THE INVENTION

This application related to methods for the treatment of acne vulgaris, commonly referred to simply as "acne."

BACKGROUND OF THE INVENTION

Acne is a commonly occurring skin disorder. It is characterized by an inflammation of the pilosebaceous unit, including the sebaceous gland. Acne lesions can take the form of comedones, papules, pustules, or nodules. Acne lesions typically appear on the face, but also occur on the back, chest and shoulders. Acne lesions are associated with *Propionibacterium acnes* (*P. acnes*). Growth of *P. acnes* is thought to be associated with, if not the cause of, the inflammatory component of acne.

The severity of acne varies widely from individual to individual, and also varies over time for any given individual. Even mild cases of acne can be cosmetically unappealing and at times disfiguring. Occasionally, acne lesions heal but leave permanent scars which are themselves sometimes prominent and permanently disfiguring.

There are a variety of treatments available for acne. Oral antibiotics (e.g. minocycline) may be used to reduce the population of *P. acnes*. Other oral antibiotics, such as doxycycline, have been used to treat acne when used at concentrations too low to have an antibiotic affect on *P. acnes*, but high enough to exert an anti-inflammatory action on the acne lesions. Topical retinoids, such as tretinoin, and topical antibiotics, such as clindamycin or azelaic acid, have also been used. In female patients, oral contraceptives have been observed to have an anti-acne effect, and are sometimes prescribed for that purpose. Orally administered isotretinoin is highly effective, but is known to produce a wide array of side effects, including sometimes severe psychiatric effects. Exposure to light, whether in the form of sunlight, or specific wavelengths of light, has also been shown to have a beneficial effect in the treatment of acne.

None of these treatments are compellingly effective, some have undesirable side effects, and all are subject to diminished effectiveness due to poor patient compliance—a common occurrence in the affected age group.

Photodynamic therapy (PDT) is an established therapeutic method for certain disorders. PDT is characterized by the use of (1) a phototherapeutic agent and (2) light. The phototherapeutic agent is applied or provided to the tissue or organ of interest. The light is used to cause a reaction (such as photoexcitation) in either the phototherapeutic agent, or in a metabolite of the phototherapeutic agent, or in a compound produced in response to the presence of the phototherapeutic agent (the activation reaction). This reaction results in a therapeutic effect.

Early phototherapeutic agents included porphyrins such as hematoporphyrin IX, hematoporphyrin derivative, or other such molecules, including Photofrin II.

The pioneering work of Kennedy & Pottier resulted in the discovery of the use of aminolevulinic acid (ALA) as a phototherapeutic agent. ALA is a precursor to a naturally occurring molecule—protoporphyrin IX. Exposing skin to light activates protoporphyrin IX in the skin. That is, the light excites or causes a reaction in the protoporphyrin IX molecule that results in the formation of reactive free radicals. Naturally occurring protoporphyrin IX can be activated by exposure to light, but occurs in quantities too small to cause any serious effect in normal tissue. By administering exogenous ALA, cells and tissues can be caused to produce greatly increased amounts of protoporphyrin IX. The resulting high concentrations of protoporphyrin IX can result in the generation of fatal quantifies of free radicals in the target cells/tissue when protoporphyrin IX is activated by exposure to light.

Kennedy & Pottier found that ALA-induced production of protoporphyrin IX made it possible to use PDT in the treatment of several disorders of metabolically active tissues. This technology has been used in the successful commercial product Levulan®, produced by Dusa Pharmaceuticals, and which has been approved by the U.S. FDA for the treatment of actinic keratoses.

Kennedy and his co-workers believed that ALA-based PDT could be used to treat acne, although they did not report any clinical resolution of acne by this method. See, U.S. Pat. No. 5,955,490. Also, they reported that the ability of light to excite protoporphyrin IX in acne lesions disappeared within 24 hours.

Kennedy reported that the ability of light to excite protoporphyrin IX in skin having acne lesions could persist to 24 hours if an occlusive covering was placed over the skin, but found that when this was done the surrounding healthy skin had as much free-radical generating protoporphyrin IX as did the acne lesions. As Kennedy contemporaneously reported, a phototherapeutic agent must have "a high degree of specificity" for the target tissue. Kennedy, J. C. "*Phtochemotherapy-Clinical Aspects*" NATO ASI Series, Springer-Verlag at p. 462 (1988). Kennedy's observation of the presence of equal amounts of protoporphyrin IX in acne lesions and in surrounding normal tissue is not specific at all.

Other workers in this field persisted in attempts to employ ALA-based PDT in the treatment of acne. See, U.S. Pat. No. 6,897,238 to Anderson. Anderson used ALA based PDT to treat acne in a small group of patients and taught that light must be applied to the skin within 1 to 12 hours after application of ALA to the skin containing acne lesions, preferably about three hours after application of the ALA.

Anderson's use of a 1 to 12 hour, and preferably a 3 hour waiting period between ALA application and exposure to light was consistent with what was by then the generally accepted timeline of ALA metabolism and protoporphyrin IX production. Research by Kennedy & Pottier showed that ALA was metabolized in mouse skin to result in peak protoporphyrin IX concentration in about six hours, with protoporphyrin levels returning to near pretreatment baseline in about 18 hours. Pottier et al, *Photochemistry and Photobiology*, Vol. 44, No. 5, pp. 679-87 (1986).

These anecdotal reports of the use of ALA-based PDT to treat acne were eventually followed by a full scale clinical trial on a group of patients large enough to provide statistically meaningful comparisons between the effectiveness of ALA-based PDT on one hand, and exposure to light alone on the other. The result of this clinical trial is available at www.clinicaltrials.gov, NCT 00706433. In this study ALA was applied to skin presenting acne lesions 45 minutes before exposure to activating light. This clinical trial determined that the use of ALA-based PDT produced results that were statistically indistinguishable from the use of light alone. That is, the ALA-based PDT had no effect.

An eight week study compared the effectiveness of ALA-based PDT with exposure to light alone as a treatment for acne. This study also compared delays of 15, 60 and 120 minutes between application of ALA and the exposure to photoactivating light. Among patients where the delay was either 15 or 120 minutes, there was no difference in the results obtained using ALA-based PDT or using light alone. For the 60 minute patients, light alone produced slightly better results than treatment with ALA-based PDT.

Thus, ALA-based PDT has not been an effective treatment for acne.

There exists a need to find a more effective way to utilize ALA-based PDT in the treatment of acne.

SUMMARY OF THE INVENTION

The inventors have discovered that in order for ALA-based PDT to be successfully used in the treatment of acne, the application of light after the application of ALA to the skin should be delayed by at least 12 hours, and possibly as long as 36 hours. An interval of 24 hours between application of ALA to the skin and exposure to light can result in optimal anti-acne therapy.

DETAILED DESCRIPTION OF THE INVENTION

In the method of this invention, ALA-based PDT is used to treat acne by applying an ALA compound to skin having acne lesions, and then waiting at least 12 hours before applying light to the skin to activate the resulting protoporphyrin IX. By that time, the ALA-induced protoporphyrin IX has not only persisted in the skin, but has localized in effective concentrations in the pilosebacious unit.

The data below shows that the ALA-based PDT method of this invention provides an effective treatment for acne. Contrary to the experience of the prior art in using various ALA-based PDT methods to treat acne, the method of this invention is effective, and, to a much greater degree, has the required specificity for acne lesions. This remarkably different and highly desirable result is obtained by departing from the conventional belief that ALA-induced protoporphyrin IX is largely dissipated within 12 hours.

The post-application waiting period before light exposure should be from about 12 to 48 hours, although waiting periods of 12 to 36 hours, 18 to 36 hours, 18 to 24 hours or 24 to 36 hours are preferred.

Derivatives of ALA, including alkylated derivatives of ALA, can also be used. These include $C_1$ to $C_8$ alkyl derivatives of ALA such as methyl ALA and hexyl ALA.

Topical formulations suitable for use in ALA-based PDT are well known in the art. These include ALA and its pharmaceutically acceptable salts, such as ALA hydrochloride and sodium ALA. Any topical vehicle that delivers ALA to the skin so that it can be taken up by the acne lesions can be used. Levulan® ALA is a formulation that is commercially available and suited to use in this invention.

The concentration of ALA in the topical formulation can range from 1 to 30 percent. Concentrations within this range can be selected on the basis of the volume of the formulation to be applied, the number of acne lesions, the general sensitivity of the patient's skin, and other clinical factors well known to practitioners, and well within the scope of good clinical judgment. Concentrations in the range of 5 to 20 percent are most useful, within 20 percent ALA being particularly useful.

The ALA can be applied to the skin by any of the conventional application techniques known in the art, such as swabs, brushes, cotton balls, gauze pads or the like. The Kerastick® application sold by DUSA Pharmaceuticals can also be used.

Light sources suitable for use in ALA-based PDT are also well known and generally available. The wavelengths of light that are capable of penetrating the skin and exciting the protoporphyrin IX molecule are well known to those skilled in the art. Devices capable of providing such light are also readily available, such as the BLU-U® illuminator. The BLU-U emits 417 nm blue light, a wavelength capable of activating protoporphyrin-IX, at a power density of 10 mW/cm$^2$.

Example 1

A 20 percent ALA Topical Solution (Levulan® Kerastick® (aminolevulinic acid HCl) was applied to a healthy female volunteer exhibiting mild to moderate acne vulgaris of the face. The subject's acne consisted primarily of inflammatory lesions (papules and pustules), however, non-inflammatory lesions (comedones) were also present in small numbers. Prior to application of the ALA solution, the subject's face was washed with soap and water and then dried. Two applications of ALA solution were applied to all exposed skin areas on the patient's face except for the immediate periorbital area. The ALA solution was allowed to dry for several minutes between applications. The subject was instructed to avoid exposure to sunlight or bright indoor light prior to returning for light activation and the subject was informed that sunscreens alone would not protect against exposure to light. The subject was undergoing no other treatment for acne at this time.

The subject returned approximately 30 hours after application of the ALA solution for light treatment using a BLU-U®, photodynamic therapy illuminator. Total light exposure time was 1000 seconds. The subject noted mild stinging and burning during the treatment, none of which was sufficient to cause interruption or cessation of the light exposure.

The subject was evaluated pre and post light exposure. Pre-light exposure examination noted that the inflammatory acne lesions appeared slightly more erythematous than at baseline (ALA solution application). Post-light treatment evaluation revealed increased erythema in the inflammatory acne lesions compared with pre-light treatment. Non-inflammatory lesions appeared to be similar to baseline both pre and post light exposure.

The subject was evaluated approximately 24 hours after light treatment. Punctate moderate erythema was noted in the inflammatory lesions with mild erythema and edema extending slightly into the perilesional skin. Erythema and edema in the inter-lesional skin areas was largely absent.

The subject was evaluated 3 weeks post light treatment. A significant reduction in the number and severity of acne lesions was noted. All but two of the inflammatory lesions present at baseline had resolved. The remaining lesions exhibited slight erythema in the lesion itself with no perilesional edema or erythema. The subject was satisfied with the reduction in acne provided by the treatment.

The invention claimed is:

1. A method of treating acne in a person in need of such treatment, the method comprising:

(i) applying a photodynamic agent topically to a portion of skin having acne lesions, wherein the photodynamic agent is aminolevulinic acid hydrochloride;

(ii) waiting 24 to 36 hours beginning upon application of the photodynamic agent, during which the portion of skin is not exposed to light; and (iii) subjecting the portion of skin to a light treatment 24 to 36 hours after application of the photodynamic agent, wherein the light treatment comprises a light wavelength within the absorption spectrum of protoporphyrin IX.

2. The method of claim 1, wherein the light wavelength is from 400 nm to 430 nm.

3. The method of claim 1, wherein the light wavelength is from 600 nm to 650 nm.

4. The method of claim 1, wherein the light treatment is in the amount of at least 10 Joules/cm$^2$.

5. The method of claim 1, wherein the light treatment has a duration of approximately 1000 seconds.

6. The method of claim 1, wherein the photodynamic agent is further applied to skin surrounding the portion of skin having acne lesions.

7. The method of claim 1, wherein step (i) comprises a first topical application of the photodynamic agent and a second topical application of the photodynamic agent, wherein the first topical application is allowed to dry prior to the second topical application.

8. The method of claim 1 further comprising the step of instructing the person to avoid exposing the portion of skin to sunlight or bright indoor light after step (i).

9. A method of treating acne in a person in need of such treatment, the method comprising:

(i) applying a topical composition to a portion of skin having acne lesions, wherein the topical composition comprises aminolevulinic acid hydrochloride;

(ii) waiting for a period of time beginning after applying the topical composition to the portion of skin and preventing exposure of the portion of skin to light during the period of time, wherein the period of time is 24 to 36 hours; and (iii) exposing the portion of skin to light from an illuminator device 24 hours to 36 hours following performance of step (i), and wherein the light from the illuminator device is of a wavelength from 600 nm to 650 nm.

10. The method of claim 9 wherein the aminolevulinic acid hydrochloride is present in the topical composition at a concentration in the range of 1% to 30%.

11. The method of claim 9 wherein the aminolevulinic acid hydrochloride is present in the topical composition at a concentration in the range of 5% to 20%.

12. The method of claim 9, wherein the topical composition is further applied to skin surrounding the portion of skin having acne lesions.

13. The method of claim 9, wherein the light from the illuminator device is in the amount of at least 10 Joules/cm$^2$.

14. A method of treating acne in a person in need of such treatment, the method comprising:

(i) applying a topical composition to a portion of skin having acne lesions, wherein the topical composition comprises aminolevulinic acid hydrochloride;

(ii) preventing exposure of the portion of skin to light for a period of time upon completion of step (i), wherein the period of time is 18 to 36 hours;

(iii) waiting for the period of time upon completion of step (i); and (iv) exposing the portion of skin to light from an illuminator device 18 hours to 36 hours following step (i).

15. The method of claim 14, wherein the exposure of step (iv) is approximately 1000 seconds.

16. The method of claim 14, wherein in step (iv) the light is in the amount of at least 10 Joules/cm$^2$.

17. The method of claim 14, wherein the topical composition is applied to skin surrounding the portion of skin having acne lesions.

18. The method of claim 14, wherein step (i) comprises a first application of the topical composition and a second application of the topical composition, wherein the first topical application is allowed to dry prior to the second topical application.

* * * * *